United States Patent [19]
Fuller et al.

[11] Patent Number: 5,807,390
[45] Date of Patent: *Sep. 15, 1998

[54] LIGHT ENERGY EMITTING PROBE WITH LIGHT-AFFECTING INCLUSIONS DISTRIBUTED THROUGHOUT

[75] Inventors: Terry A. Fuller, Rydal, Pa.; Arthur Lompado, Newark, Del.; Mark A. DeStefano, Perkasie, Pa.

[73] Assignee: Surgical Laser Technologies, Inc., Montgomeryville, Pa.

[*] Notice: The term of this patent shall not extend beyond the expiration date of Pat. No. 5,520,681.

[21] Appl. No.: 559,359

[22] Filed: Nov. 16, 1995

Related U.S. Application Data

[63] Continuation of Ser. No. 187,359, Jan. 26, 1994, Pat. No. 5,520,681, which is a continuation of Ser. No. 874,282, Apr. 24, 1992, abandoned.

[51] Int. Cl.⁶ .................................................. A61B 17/36
[52] U.S. Cl. .............................. 606/17; 606/13; 606/15
[58] Field of Search ........................... 606/10–13, 14–17, 606/27, 28; 607/89

[56] References Cited

U.S. PATENT DOCUMENTS

| | | |
|---|---|---|
| 4,539,987 | 9/1985 | Nath et al. .................................. 606/14 |
| 4,592,353 | 6/1986 | Daikuzono . |
| 4,676,231 | 6/1987 | Hisazumi et al. . |
| 4,693,244 | 9/1987 | Daikuzono ................................ 606/16 |
| 4,736,743 | 4/1988 | Daikuzono . |
| 4,832,024 | 5/1989 | Boussignac et al. . |
| 4,911,712 | 3/1990 | Harrington . |
| 5,074,861 | 12/1991 | Schneider et al. . |
| 5,209,748 | 5/1993 | Daikuzono . |
| 5,348,552 | 9/1994 | Nakajima et al. ........................ 606/13 |
| 5,520,681 | 5/1996 | Fuller et al. .............................. 606/17 |

FOREIGN PATENT DOCUMENTS

| | | |
|---|---|---|
| 64782/90 | 4/1991 | Australia . |
| PCT/JP89/01243 | 12/1989 | WIPO . |
| PCT/JP90/00040 | 9/1990 | WIPO . |
| PCT/JP90/01079 | 9/1990 | WIPO . |
| PCT/JP90/01122 | 9/1990 | WIPO . |

*Primary Examiner*—Michael Peffley
*Attorney, Agent, or Firm*—Seidel, Gonda, Lavorgna & Monaco, PC

[57] ABSTRACT

A probe for medical use includes a tip portion having a light energy input region for receiving light energy from a light source and a predetermined light energy output region whereby tissue subtended by the region may be irradiated by the light energy. The tip portion consists essentially of light propagating material having inclusions distributed therein for interacting with the light energy to produce a predetermined light energy output pattern. The light propagating material is a light propagating inorganic compound.

29 Claims, 2 Drawing Sheets

LIGHT ENERGY EMITTING PROBE WITH LIGHT-AFFECTING INCLUSIONS DISTRIBUTED THROUGHOUT

This is a continuation Ser. No. 08/187,359 filed on 26 Jan. 1994, now U.S. Pat. No. 5,520,681, which is a continuation of Ser. No. 07/874,282 filed on 24 Apr. 1992 (abandoned).

FIELD OF THE INVENTION

The present invention relates to medical devices for use in medicine and surgery in which the probe conveys light energy to tissue to be treated by the probe. (As used herein, the term "treated" means exposed to light energy for any purpose, including but not limited to phototherapy, biostimulation, incision, vaporization, coagulation, and the like.)

BACKGROUND OF THE INVENTION

Light energy, including but by no means limited to laser light energy, has been used in medicine and surgery for many years. Different wavelengths of light interact differently with tissue, so tissue effects are wave-length-dependent. Tissue effects are also dependent upon the amount of energy, expressed as joules (J). Energy is the product of power, in watts, and duration of exposure, in seconds. The power density (power divided by area) applied to the tissue is a variable frequently controlled by the physician. power density is, in turn, a function of the distribution pattern of light energy applied to the tissue from a light source or light-emitting member of an optical delivery system.

Lasers in particular are used in many different types of medical procedures. Different lasers cause different tissue effects, depending upon the wavelengths of the laser emission. Among the types of lasers used in laser medicine are the $CO_2$ laser, the KTP laser and the neodymium:YAG laser. In addition to laser light sources, which are referred to as "coherent," non-laser or "incoherent" light sources may also be used for medical and surgical procedures.

In order to get the light energy from the light source to the tissue to be treated, it is desirable to have a delivery system between the light source and the operative site. Such delivery systems as used in medicine and, in particular, in surgery can be broadly divided into those which either contact or do not contact tissue to be treated. In non-contact delivery systems, the distal end of the delivery system does not touch the tissue but, instead, uses a fiber optic or other light guide means to conduct light energy from a light source to a location adjacent, but not touching, the tissue. The light energy passes from the distal end of the delivery system through a gas or a liquid before reaching the tissue. In addition to non-contact procedures, techniques and devices have been developed in which the distal end of the delivery system comes into physical contact with the tissue.

In both contact and non-contact procedures, different tissue effects can be achieved by using different output energy distributions from the delivery system. One way of varying the output energy distribution is to vary the size and shape of the distal end of the delivery system. Another is to provide structure or coatings on the distal end which absorb, scatter, or both absorb and scatter, energy from the light source in a controlled and predictable manner before it reaches the tissue.

U.S. Pat. No. 4,693,244 discloses a medical and surgical laser probe in which the distal end of the probe is tapered so as to emit laser radiation from the tip end face of the tapered portion without leaking it out from the tapered portion. Such a structure is highly effective for incising tissue because it provides a high power density at the end face of the tapered portion. However, the laser probe described in the '244 patent is also useful in other procedures where a more diffuse energy density is desired. Thus, in an alternate embodiment of the invention disclosed in the '244 patent, the end face has formed on it a curved surface, which includes numerous fine bubbles which diffuse laser radiation emitted from the end face. The diffusion pattern can be varied by varying the curvature of the surface. Consequently, a delivery system incorporating a curved surface with numerous fine bubbles therein can be used for a number of surgical procedures in which scattered laser radiation from the probe is desirable.

In the embodiment of the '244 patent which uses a curved surface with numerous fine bubbles therein, the larger the curvature the greater the diffusion angle of the laser radiation. Also, ideally the bubbles should be of a uniform shape and size. If the bubbles are too large, the laser energy will be reflected in undesirable directions (e.g., back toward the fiber optic). The number and distribution of bubbles should be such that the tip is translucent, with a light transmission of between 20 and 50 percent. The '244 patent points out that if there are too many bubbles, and consequently the transmission of laser radiation is decreased, too much of the laser energy may be lost to heat. Thus, according to the '244 patent, it is possible that, in use, the temperature of the tip may exceed the maximum operating temperature for the material from which the tip is manufactured. This can cause the tip to deform and alter its physical shape and characteristics.

Currently, contact probes are manufactured primarily from one (or both) of two materials, sapphire ($Al_2O_3$) and/or quartz. Sapphire is preferred in many cases because it has a useful working temperature up to 1800° C., with a melting point of 2040° C. In contrast, the maximum useful working temperature for quartz is approximately 900° C., and its melting point is only 1600° C. Laser surgical procedures can result in the tip end reaching temperatures in excess of 1000° C., which can cause quartz tip ends to deform and alter their physical shape. A change in the shape of the tip end can change the power density at the tip end and the power distribution profile, which alters the clinical effect of the tip. Moreover, sapphire can be used as a mechanical tool in addition to a laser energy transmission device. Sapphire has a Young's modulus of $5.3 \times 10^7$ psi, whereas the Young's modulus of fused silica is only $1.02 \times 10^7$ psi. Because of this, a tip made from fused silica used in a mechanical mode exhibits a much greater potential for breakage.

One the other hand, sapphire is more susceptible to thermal shock than is fused silica. Thermal shock can occur when the temperature of a material changes very rapidly. Such a rapid temperature change induces physical changes inside the tip end which can cause a sapphire tip to check or shatter. One indicator of a material's resistance to thermal shock is its coefficient of thermal expansion. For sapphire, this coefficient is $7.7 \times 10^{-6}$ cm/cm° C., at 40° C., whereas for fused silica this coefficient is $0.55 \times 10^{-6}$ cm/cm° C. at 40° C. As stated above, laser surgical procedures can result in extremely high tip end temperatures, which can lead to thermal shock problems. Hence, there may be some procedures where fused silica is an acceptable, or even the preferred alternative to, sapphire.

In addition to fused silica and sapphire, tips fabricated from resins have been proposed. Resin tips are relatively easy to fabricate into structures of various shapes and which contain light absorbing and/or light reflecting particles. The type and distribution of particles, as well as the shape of the tip, affect the output energy distribution of those tips. Resin tips, however, are limited to low-temperature uses, since the temperatures at which resins will plastically deform and melt are quite low in comparison to fused silica and sapphire. Resin tips tend also to be much softer than fused silica and sapphire, and therefore lack the mechanical strength required of a tip in some procedures. Also, some resin tips, when overheated, can burn and emit toxic fumes.

The present invention aims to overcome the disadvantages of prior delivery systems while retaining their respective advantages.

SUMMARY OF THE INVENTION

The present invention is broadly directed to a probe for medical use. The probe comprises a tip portion having a light energy input region for receiving light energy from a light source and a predetermined light energy output region whereby tissue subtended by said region may be irradiated by said light energy. The tip consists essentially of light propagation material having inclusions distributed therein for interacting with said light energy to produce a predetermined light energy output pattern. The light propagating material is a light propagating inorganic compound.

The present invention provides a probe in which light energy may be absorbed or scattered in all directions, or both, as it traverses the tip portion. Thus, the laser energy is not focused as it traverses the tip portion, as it is, for example, in the device of U.S. Pat. No. 4,693,244. Instead, it may be either absorbed or emitted from the tip portion in a diffuse but highly-predictable manner, or both.

DESCRIPTION OF THE DRAWINGS

For the purpose of illustrating the invention, there is shown in the drawings a form which is presently preferred; it being understood, however, that this invention is not limited to the precise arrangements and instrumentalities shown.

DESCRIPTION OF THE INVENTION

Figure 1:
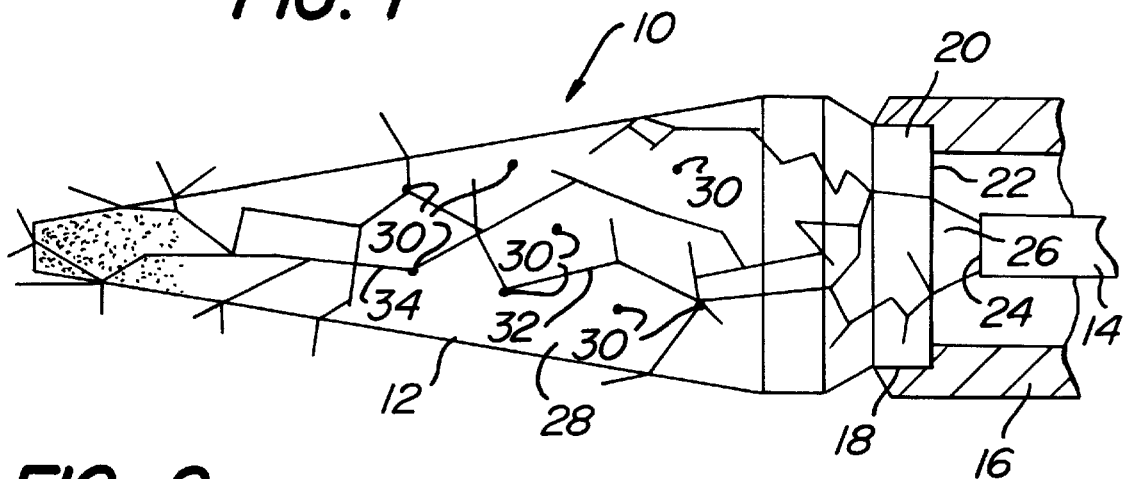
FIG. 1 is a simplified illustration of a probe according to the invention, illustrating the tip portion and the propagation of light energy through and from it.

Referring now to the drawings, wherein like numerals indicate like elements, there is shown in FIG. 1 a probe 10 in accordance with a first embodiment of the present invention. Probe 10 comprises a tip portion 12 and a light guide 14 for conducting light energy from a light source (not shown) to tip portion 12. preferably, light guide 14 is a fiber optic or other flexible light guide means. Light guide 14 may be contained within a supporting means 16, which may be in the form of a thin walled, hollow tube. Supporting means 16 may conveniently be provided with a recessed counterbore 18 for receiving and retaining tip portion 12. Tip portion 12 may accordingly be provided with a cylindrical shank portion 20 which may be received in counterbore 18. Shank portion 20 has a generally planar face 22 which receives light energy form the output face 24 of light guide 14. As shown in FIG. 1, there is a small gap 26 between faces 22 and 24, although a gap is not necessary as will be seen in connection with further embodiments of the invention to be described below.

Tip portion 12 consists essentially of light propagating material 28. Light propagating material 28 is an inorganic compound, and includes inorganic oxides, such as glasses (e.g., fused silica ($SiO_2$)), and ceramics, such as aluminum oxide ($Al_2O_3$). The ceramics may include dopants such as magnesium (Mg) and chromium (Cr). Light propagating material 28 also includes other inorganic compounds such as zinc selenide (ZnSe), zinc sulfide (ZnS) and the like. The light propagating material 28 is preferably aluminum oxide ($Al_2O_3$), also known as sapphire. Sapphire is preferred because it is physiologically neutral, has high mechanical strength, high hardness, high light transmission, excellent thermal resistance and high thermal conductivity, and exhibits low tissue adhesion when used in contact procedures.

In certain procedures, temperatures above 1000° C. are encountered, and thus light propagating material 28 should be capable of withstanding such temperatures. For example, one such procedure is the use of a laser to vaporize tissue for surgery. In other procedures, temperatures as low as physiological temperature (body temperature) are encountered. Examples of such procedures include photodynamic therapy and biostimulation. Many additional procedures span the temperature range between these two extremes.

An important feature of light propagating material 28 is that it contains inclusions 30 distributed throughout the material for interacting with light energy fed into tip portion 12 from light guide 14. In FIG. 1, only a few inclusions, sufficient to illustrate the invention, are shown. Inclusions 30 may interact with light energy, represented in FIG. 1 by rays 32 and 34, to identify only two rays, by scattering the light energy or by absorbing the light energy, or both. That is, the inclusions 30 may be of a type that scatters light energy without significant absorption, or a type that absorbs light energy without significant scattering, or may comprise both types. Types of inclusions that tend to scatter more than absorb light energy include reflective metal particles such as aluminum, gold or similar metals, or even transparent materials with refractive indexes different from the refractive index of the light propagating material 28, such as diamond, zirconium oxide, and like materials. In addition, inclusions that tend to scatter rather than absorb light energy may be grain boundaries of a polycrystalline material such as zinc selenide (ZnSe). Types of inclusions that tend to absorb rather than scatter light energy include particles of carbon or graphite, iron oxide, manganese dioxide, and like materials. Either one or both types of inclusions may be present in light propagating material 28, as may be desired. Thus, if a relatively low temperature, high scatter probe is desired, only inclusions that scatter rather than absorb light energy will be preferred. Where it is desired to have a probe that operates at a very high temperature, only inclusions that absorb rather than scatter light energy will be preferred.

A preferred material for light propagating material 28 is a form of aluminum oxide sold under the trade name "Lucalox." This material has a purity of 99.9% aluminum oxide and is free of intentionally-introduced materials or dopants. This material has inclusions in the form of porosity and grain boundaries, which act to scatter light energy without appreciable absorption.

Another suitable material for light propagating material 28 is a quartz product sold commercially under the trade name "Gelsil." This material is a high purity (greater than 99%) porous silica ($SiO_2$) material with internal voids ranging in size from 25 to 200 Angstroms, which scatter light energy without significant absorption. Although this material, being quartz, is not as tough as aluminum oxide, and does not possess the high temperature characteristics of aluminum oxide, it may be suitable for many lower temperature, lower mechanical stress applications, or in applications in which the probe may have a sufficient size to provide the required mechanical strength.

Dopant materials can be intentionally introduced into light propagating material 28 to absorb light energy. Such light energy absorbing dopant materials may be introduced instead of, or in addition to, light scattering inclusions. Materials such as carbon or manganese dioxide ($MnO_2$), to name only two, may be used as light energy absorbing dopants.

As shown in FIG. 1, light energy will be scattered from all surfaces of tip portion 12 due to the presence of inclusions 30, which scatter the light energy. Thus, light energy entering planar face 22 of tip portion 12 will immediately encounter light scattering inclusions 30, with the result that light energy will be emitted in a distribution pattern in all directions around the entire outer surface of tip portion 12. The distribution pattern illustrated in the figures herein is for an optically clear light propagating medium, such as, for example, air, saline or water. The distribution pattern may be changed, however, by locating the output face of the light guide within the tip portion of the probe.

Figure 2:
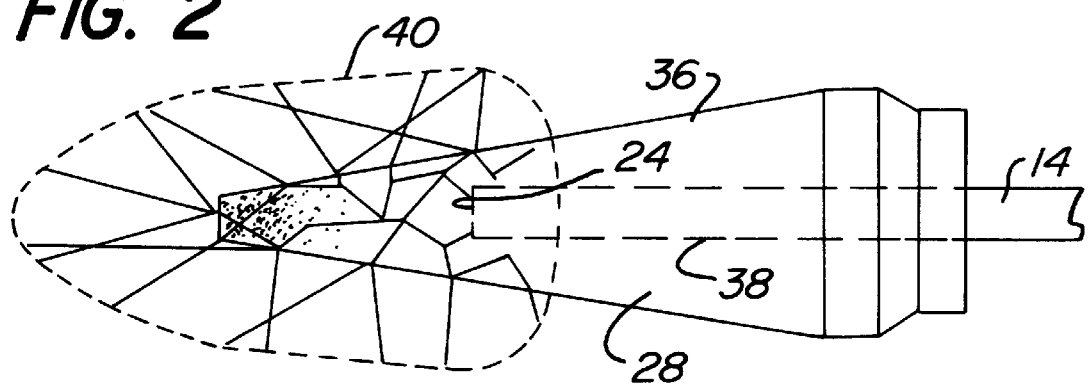
FIG. 2 is a simplified illustration of a probe according to a second embodiment of the invention.

For example, referring now to FIG. 2, tip portion 36 as shown in FIG. 2 is substantially identical to tip portion 12 shown in FIG. 1, except that tip portion 36 has an axial bore 38 therein for receiving light guide 14. Thus, output face 24 of light guide 14 is located within and surrounded by light propagating material 28 of tip portion 36. Because output face 24 is located within light propagating material 28, most of the light energy conveyed to tip portion 36 by light guide 14 can be emitted from the forward end of tip portion 36, within the volume defined by the dashed envelope 40 in FIG. 2. Thus, in the embodiment illustrated in FIG. 2, the probe has a light energy output pattern in which most of the light energy is emitted from the forward end of tip portion 36. The light energy output pattern of this embodiment peaks at the axis of tip portion 36 and decreases in radial directions away from the axis.

Figure 3:
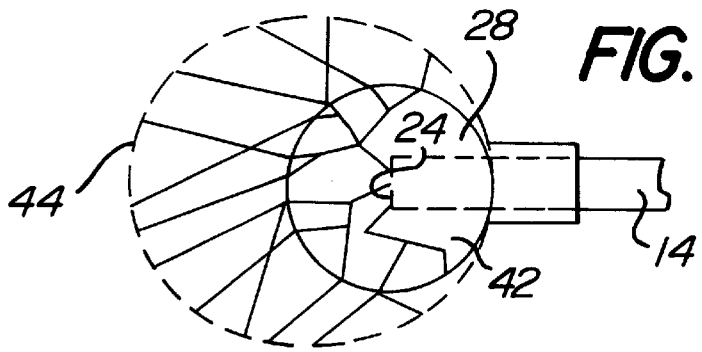
FIG. 3 is a simplified illustration of a probe according to the invention, having a spherical shape.

The tip portion may have many shapes. Thus, for example, as shown in FIG. 3, a generally spherical tip portion 42 may be provided. As with tip portion 36, tip portion 42 may be provided with a bore 38 for receiving light guide 14 therein. The shape shown in FIG. 3 can give a light energy output pattern defined by envelope 44. Envelope 44 defines a generally spherical light energy output pattern in which light energy is generally forwardly directed from tip portion 42.

Figure 4:
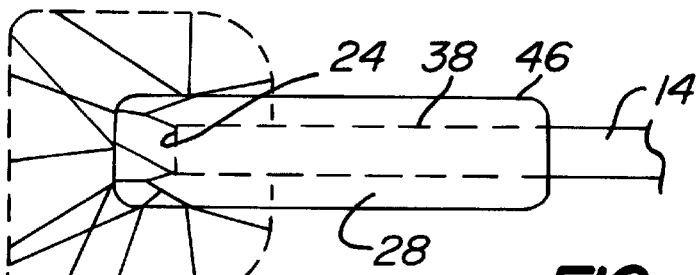
FIGS. 4 and 5 are a simplified illustrations of a probe according to the invention, having a generally cylindrical shape, but different output distribution patterns.

FIG. 4 illustrates a shape of a probe tip portion 46 according to the invention in which the energy distribution is relatively constant over a circular area in a plane perpendicular to the axis of the tip portion, as shown by envelope 48. In FIG. 4, tip portion 46 is generally cylindrical in shape. As with tip portion 36, tip portion 46 may be provided with a bore 38 for receiving light guide 14 therein.

Figure 5:
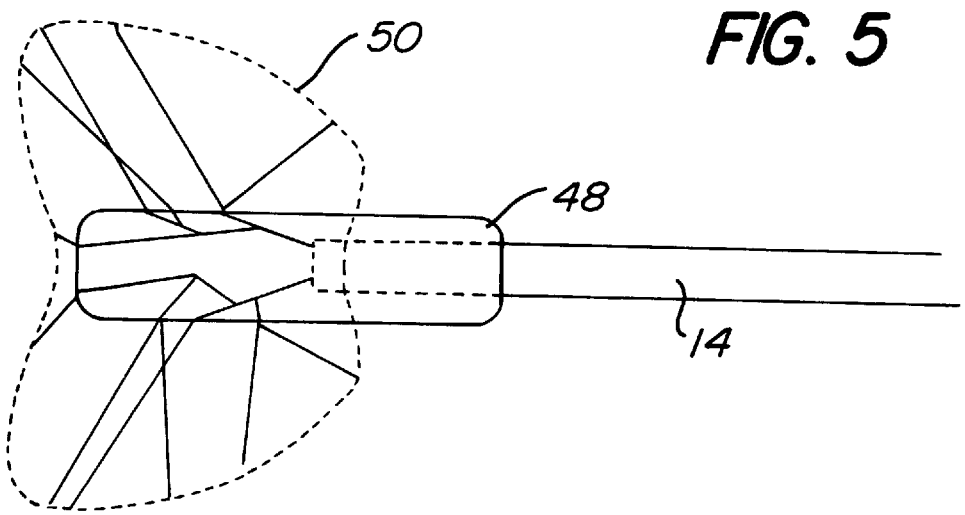

The light energy distribution pattern can be modified not only by altering the shape of the tip portion, but by altering the extent to which light guide 14 extends into the interior of the tip portion. For example, as shown in FIG. 5, tip portion 48 is the same shape as tip portion 46 shown in FIG. 4. However, as seen by comparing FIGS. 4 and 5, light guide 14 extends into tip portion 48 for a much shorter distance than light guide 14 extends into tip portion 46. This results in a light distribution pattern which is generally more conical in shape, as shown by envelope 50. The light energy distribution pattern thus not only depends on the shape of the tip portion, but on the extent to which light guide 14 extends into the tip portion.

Figure 6:
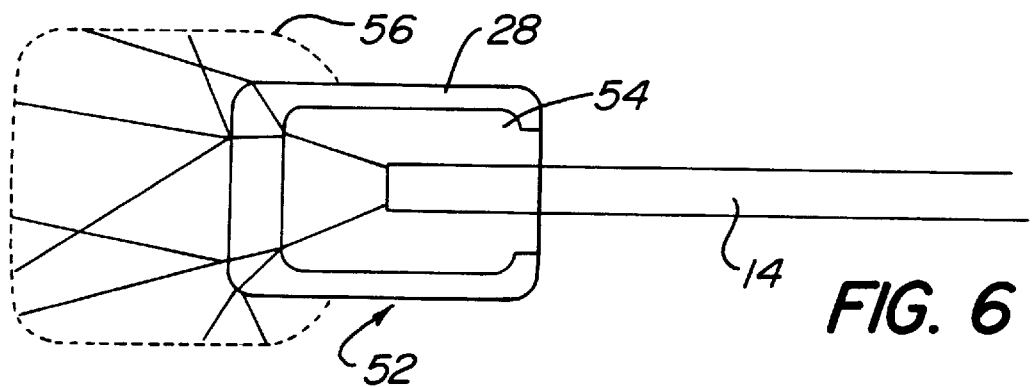
FIG. 6 is a simplified illustration of a probe according to still another embodiment of the invention.

FIG. 6 illustrates still another embodiment of the invention, in which the light propagating material 28 is located on only the surface of tip portion 52. Thus, tip portion 52 comprises an optically clear material 54 surrounded by light propagating material 28. Optically clear material 54 may be any suitable optically clear material, such as any of the materials already mentioned, including aluminum oxide, or the like. Preferably, however, optically clear material 54 is air, in which event tip portion 52 is in the form of a generally hollow shell surrounding light guide 14. Alternatively, tip portion 52 can be a composite monolithic material with light propagating material 28 being a scattering portion and optically clear material 54 being an optically transmissive portion. In this embodiment, the light energy distribution pattern is illustrated by envelope 56.

Figure 8:
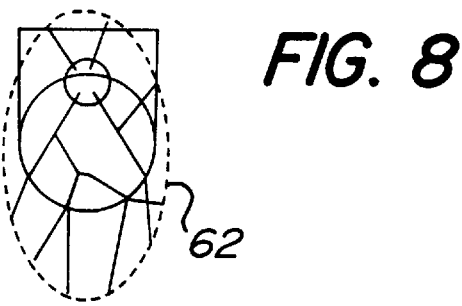
FIG. 8 is a front view of the probe of FIG. 7.
Figure 7:
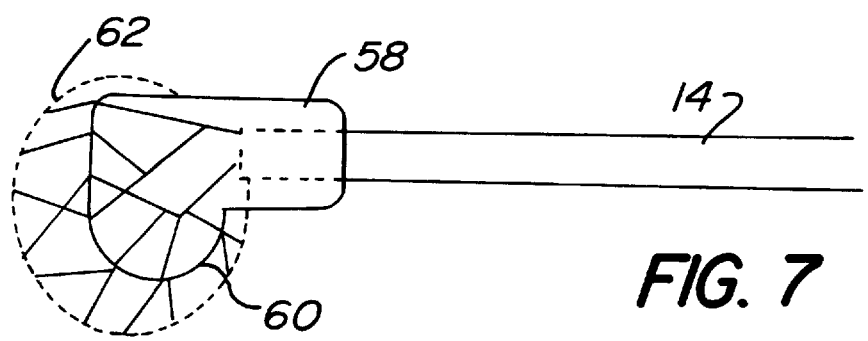
FIG. 7 is a simplified illustration of a probe according to the invention, having an asymmetrical shape.

Still another shape of the tip portion according to the present invention is illustrated in FIGS. 8 and 9. The shape illustrated in FIGS. 8 and 9 is an asymmetrical shape which comprises a generally cylindrical portion 58 having a spherical projection 60 on one side of the axis of generally cylindrical portion 58. Light guide 14 is located generally coaxial with the axis of cylindrical portion 58. The shape illustrated in FIGS. 7 and 8 gives a light energy distribution pattern indicated by envelope 62 which is asymmetric with respect to the axis of light guide 14. This shape permits surgical procedures either in front of or lateral to the axis of light guide 14.

It should be understood that, although several different shapes have been shown for purposes of illustrating the invention, other shapes may be employed without departing from the scope of the present invention.

The light energy distribution pattern can also be changed as a function of light-scattering inclusions in the light propagating material. Thus, a large number of such inclusions would yield a highly-diffuse distribution pattern, while a smaller number of such inclusions would yield a more concentrated distribution pattern.

The present invention may be embodied in other specific forms without departing from the spirit or essential attributes thereof and, accordingly, reference should be made to the appended claims, rather than to the foregoing specification, as indicating the scope of the invention.

We claim:

1. A probe for medical use, said probe comprising a tip portion having a light energy input region for receiving light energy from a light source and a predetermined light energy output region whereby tissue subtended by said light energy output region may be irradiated by said light energy, said tip portion consisting essentially of light propagating material having inclusions distributed therein and generally throughout said tip portion between said light energy input region and said light energy output region for interacting with said light energy to produce a predetermined energy output pattern over a wide area without significantly impairing the transmission of light energy and without significantly absorbing said light energy, said light propagating material being a light propagating inorganic compound, wherein the inclusions include microscopic voids having dimensions substantially smaller than the wavelength of said light energy.

2. A probe as in claim 1, wherein the inorganic compound is an oxide.

3. A probe as in claim 2, wherein the oxide is a ceramic.

4. A probe as in claim 3, wherein the ceramic is aluminum oxide.

5. A probe as in claim 4, wherein the aluminum oxide comprises substantially a single crystal.

6. A probe as in claim 2, wherein the oxide is a glass.

7. A probe as in claim 6, wherein the glass is fused silica.

8. A probe as in claim 1, wherein the inorganic compound is zinc selenide.

9. A probe as in claim 1, wherein said inclusions comprise means for diffusing said light energy within said tip and in a predetermined radiation pattern external to said tip.

10. A probe as in claim 1, wherein the inclusions comprise particles of at least one dopant material.

11. A probe as in claim 1, wherein said probe is adapted to be connected to a laser light source.

12. A probe as in claim 1, wherein said probe is adapted to be connected to a source of incoherent light.

13. A probe as in claim 1, wherein said light energy output region is adapted to contact tissue to be irradiated.

14. A probe as in claim 1, wherein said tip portion consists essentially of an optically clear portion and a light scattering portion.

15. A probe for medical use, said probe comprising a tip portion having a light energy input region for receiving light energy from a light source and a predetermined light energy output region whereby tissue subtended by said light energy output region may be irradiated by said light energy, said tip portion consisting essentially of light propagating material having inclusions distributed therein and generally throughout said tip portion between said light energy input region and said light energy output region for interacting with said light energy to produce a predetermined energy output pattern over a wide area without significantly impairing the transmission of light energy and without significantly absorbing said light energy, said light propagating material being a ceramic, the inclusions including microscopic voids having dimensions substantially smaller than the wavelength of said light energy.

16. A probe as in claim 15, wherein the ceramic is aluminum oxide.

17. A probe as in claim 16, wherein the aluminum oxide comprises substantially a single crystal.

18. A probe as in claim 15, wherein said inclusions comprise means for diffusing said light energy within said tip and in a predetermined radiation pattern external to said tip.

19. A probe as in claim 15, wherein the inclusions comprise particles of at least one dopant material.

20. A probe as in claim 15, wherein said tip portion consists essentially of an optically clear portion and a light scattering portion.

21. A probe for medical use, said probe comprising a tip portion having a light energy input region for receiving light energy from a light source and a predetermined light energy output region whereby tissue subtended by said light energy output region may be irradiated by said light energy, said tip portion consisting essentially of light propagating material having inclusions distributed therein and generally throughout said tip portion between said light energy input region and said light energy output region for interacting with said light energy to produce a predetermined energy output pattern over a wide area without significantly impairing the transmission of light energy and without significantly absorbing said light energy, said light propagating material being a glass, the inclusions including microscopic voids having dimensions substantially smaller than the wavelength of said light energy.

22. A probe as in claim 21, wherein the glass is fused silica.

23. A probe as in claim 21, wherein said inclusions comprise means for diffusing, said light energy within said tip and in a predetermined radiation pattern external to said tip.

24. A probe as in claim 21, wherein the inclusions comprise particles of at least one dopant material.

25. A probe as in claim 21, wherein said tip portion consists essentially of an optically clear portion and a light scattering portion.

26. A probe for medical use, said probe comprising a tip portion having a light energy input region for receiving light energy from a light source and a predetermined light energy output region whereby tissue subtended by said light energy output region may be irradiated by said light energy, said tip portion consisting essentially of light propagating material having inclusions distributed therein and generally throughout said tip portion between said light energy input region and said light energy output region for interacting with said light energy to produce a predetermined energy output pattern, said light propagating material being zinc selenide, the inclusions including microscopic voids having dimensions substantially smaller than the wavelength of said light energy.

27. A probe as in claim 26, wherein said tip portion consists essentially of an optically clear portion and a light scattering portion.

28. A probe for medical use, said probe comprising a tip portion having a light energy input region for receiving light energy from a light source and a predetermined light energy output region whereby tissue subtended by said light energy output region may be irradiated by said light energy, said tip portion consisting essentially of light propagating material having inclusions distributed therein and generally throughout said tip portion between said light energy input region and said light energy output region for interacting with said light energy to produce a predetermined energy output pattern over a wide area without significantly impairing the transmission of light energy and without significantly absorbing said light energy, said light propagating material being substantially a single crystal of aluminum oxide, the inclusions including microscopic voids having dimensions substantially smaller than the wavelength of said light energy.

29. A probe for medical use, said probe comprising a tip portion having a light energy input region for receiving light energy from a light source and a predetermined light energy output region whereby tissue subtended by said light energy output region may be irradiated by said light energy, said tip portion consisting essentially of light propagating material having inclusions distributed therein and generally throughout said tip portion between said light energy input region and said light energy output region for interacting with said light energy to produce a predetermined energy output pattern over a wide area without significantly impairing the transmission of light energy and without significantly absorbing said light energy, said light propagating material being fused silica having microscopic voids therein, said voids having dimensions substantially smaller than the wavelength of said light energy.

* * * * *